United States Patent [19]
Pujado et al.

[11] Patent Number: 5,599,956
[45] Date of Patent: Feb. 4, 1997

[54] INTEGRATED PROCESS FOR THE PRODUCTION OF PROPYLENE OXIDE

[75] Inventors: Peter R. Pujado, Palatine; John I. Hammerman, Arlington Heights, both of Ill.

[73] Assignee: UOP, Des Plaines, Ill.

[21] Appl. No.: 606,108

[22] Filed: Feb. 22, 1996

[51] Int. Cl.$^6$ .................... C07D 301/12; C07D 303/04
[52] U.S. Cl. ........................................... 549/531
[58] Field of Search ............................. 549/531

[56] References Cited

U.S. PATENT DOCUMENTS

| | | | |
|---|---|---|---|
| 5,166,372 | 11/1992 | Crocco et al. | 549/531 |
| 5,214,168 | 5/1993 | Zajacek et al. | 549/531 |
| 5,221,795 | 6/1993 | Clerici et al. | 549/531 |
| 5,354,875 | 10/1994 | Nemeth et al. | 549/531 |
| 5,384,418 | 1/1995 | Zajacek et al. | 549/531 |
| 5,463,090 | 10/1995 | Rodriguez et al. | 549/531 |

*Primary Examiner*—Joseph E. Evans
*Attorney, Agent, or Firm*—Thomas K. McBride; Eugene I. Snyder

[57] ABSTRACT

Propylene oxide may be produced by an integrated process utilizing as a basic feedstock a refinery stream containing saturated hydrocarbons. The first element of the process converts one or more of the saturated hydrocarbons to a stream containing propylene and hydrogen using steam cracking, catalytic cracking, or preferably catalytic dehydrogenation. Hydrogen and propylene are separated, and the hydrogen is employed in a reaction cycle affording hydrogen peroxide. The latter is then used to epoxidize propylene in the presence of a suitable catalyst, especially a titanosilicate.

10 Claims, 1 Drawing Sheet

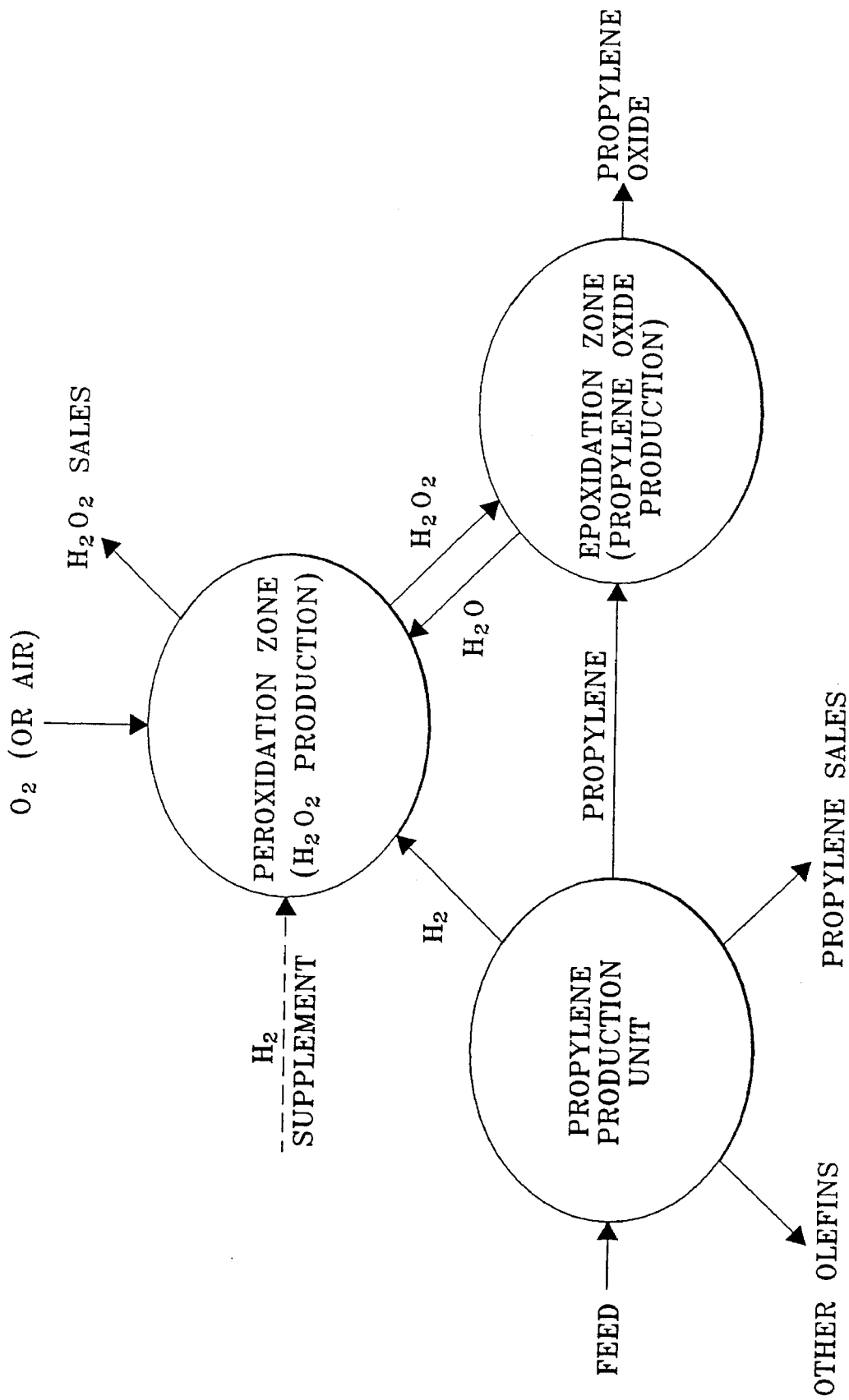

INTEGRATED PROCESS FOR THE PRODUCTION OF PROPYLENE OXIDE

FIELD OF THE INVENTION

This invention relates to the production of propylene oxide from propylene. More particularly, our invention relates to an integrated process for the production of propylene oxide by peroxidic oxidation of propylene where the propylene itself is formed from one or more paraffins or paraffinic streams typically found in refineries.

BACKGROUND OF THE INVENTION

Propylene oxide is an important article of commerce finding use in diverse areas. For example, polymerization with alcohols as initiators affords polyether polyols. Polymerization catalyzed by, e.g., ferric chloride affords poly(propylene oxide) polymers with molecular weights of 100,000 or more. Reaction with water gives a spectrum of propylene glycols, including monopropylene glycol, dipropylene glycol, tripropylene glycol, and so forth. Reaction with ammonia, or amines generally, affords aminoalcohols. Each of the foregoing are important niche commodities, either per se or as reactive components in, e.g., polyurethane manufacture.

The principal route to propylene oxide employs the so-called chlorohydrin process where propylene is first convened to its chlorohydrin and the latter is subsequently dehydrochlorinated to produce the epoxide. Chlorohydrin formation is effected by reaction of aqueous chlorine or hypochlorous acid with propylene under acidic conditions. Dehydrochlorination is accomplished by treating the chlorohydrin with a base.

More recently the oxidation of propylene with peroxide has become competitive to the traditional chlorohydrin route. In addition to hydrogen peroxide, organic peroxides may be used as the oxidant and include materials such as t-butyl hydroperoxide, t-pentyl hydroperoxide, ethylbenzene hydroperoxide, cumene hydroperoxide and peracetic acid. Where organic peroxides are used an organic byproduct necessarily is formed. For example, if t-butyl hydroperoxide is used as the oxidant t-butyl alcohol is an unavoidable byproduct and any process using this organic hydroperoxide must either find t-butyl alcohol as an economically acceptable byproduct, (i.e., its market must make the overall process economically viable) or the process must provide for recycling t-butyl alcohol to t-butyl hydroperoxide. Epoxidation catalysts generally are soluble metal compounds of, e.g., molybdenum, vanadium, tungsten, and titanium.

Although the use of hydrogen peroxide as the oxidant would be singularly advantageous, since its byproduct is water whose recycle is unnecessary, until recently commercial routes to propylene oxide have focused on the use of organic peroxides, such as t-butyl hydroperoxide and ethylbenzene hydroperoxide, and commercially successful processes based thereon have been developed. Even though the use of hydrogen peroxide as an oxidant has many attractions, one limitation is the practical need for having a hydrogen peroxide generation facility at the site, i.e., it is not commercially feasible to transport large amounts of dilute hydrogen peroxide to the oxidation site and the transport of concentrated solutions presents safety hazards. Commercial generation of hydrogen peroxide is merely the reaction of hydrogen and oxygen, although performed indirectly rather than directly. Therefore, hydrogen peroxide generation requires a source of hydrogen. Consequently, if one wishes to oxidize propylene with hydrogen peroxide it is necessary that the complex have a continual and guaranteed on-site source of hydrogen. We have recognized that the foregoing conditions can be met if propylene is formed with the coproduction of hydrogen, and that an integrated process can be devised making propylene oxide production via peroxide-based oxidation of propylene a commercial reality. The remainder of this application is devoted to a description of our invention.

SUMMARY OF THE INVENTION

Our invention is an integrated process starting with various typical refinery feeds for the production of propylene oxide via epoxidation using hydrogen peroxide. An embodiment comprises converting a paraffinic feedstream to a product stream containing hydrogen and propylene, utilizing the separated hydrogen in the formation of hydrogen peroxide and utilizing the separated propylene as a reactant in epoxidation with hydrogen peroxide. In a more specific embodiment the propylene/hydrogen product stream arises from catalytic dehydrogenation of propane. In another embodiment the reaction of hydrogen peroxide and propylene is catalyzed by a titanium silicalite. Other embodiments will appear from the following description.

DESCRIPTION OF THE FIGURES

FIG. 1 is a simplified flow diagram for the integrated process of our invention.

DESCRIPTION OF THE INVENTION

The invention herein is an integrated process using a common refinery feed to ultimately produce propylene oxide with minimal byproduct formation other than those products normally found in a refinery. Our invention is concisely summarized in FIG. 1. The remainder of this application will elaborate upon the integrated process, its elements, and various embodiments thereof. Our integrated process clearly provides three distinct elements. The first may be termed the propylene production unit and is characterized by conversion of one or more paraffins, generally part of a typical refinery stream, to a product containing propylene and hydrogen. By suitable separation processes the product stream is purified to afford a hydrogen concentrate stream and a propylene rich stream. In the second element of our invention hydrogen is reacted with oxygen, albeit indirectly, to afford hydrogen peroxide. Whether the hydrogen concentrate needs further purification prior to its use depends on many factors and FIG. 1 accommodates and includes the possibility of further hydrogen purification as a necessary or desirable adjunct incident to its use in hydrogen peroxide production. The last element of our invention is the catalytic epoxidation of propylene with hydrogen peroxide. Further purification of propylene prior to its epoxidation may be desirable or even required, although this is not generally contemplated, depending upon its mode of production and the precise nature of the epoxidation.

The first element in our invention is propylene production from a saturated hydrocarbon-containing feedstock, with accompanying formation of hydrogen as a coproduct. There are three main methods of propylene formation in this context; steam cracking, catalytic cracking and especially the subclass of fluid catalytic cracking, and propane dehydrogenation. All three of the foregoing methods share the characteristic that the reaction product contains both propylene and hydrogen, which as stated previously is a prerequisite of propylene production in our integrated process. See Ullmann's Encyclopedia of Industrial Chemistry, 5th, Completely Revised Edition, Vol. A22, pp. 213–220 (1993). The catalytic conversion of methanol or dimethyl ether to olefins affords propylene and ethylene, but no hydrogen.

Steam cracking is used primarily for the formation of ethylene but propylene is a major byproduct. See op. cit., Vol. A10, pp. 47–61 (1987). Stem cracking is essentially the pyrolysis of hydrocarbons in the presence of stem. In stem cracking a hydrocarbon stream is heated and mixed with stem to a temperature in the range of 500°–650° C. The stream then enters a reactor where it is further heated to 750°–875°, temperatures where saturated hydrocarbons in the feedstock crack into smaller molecules. The overall reaction is highly endothermic and is energy intensive. The feedstocks in steam cracking generally contain straight and branched-chain alkanes as well as naphthenes or cycloparaffins. Aromatics generally do not contribute to cracked products, i.e., products of lower molecular weight, but often are present in the feedstream which typically is produced elsewhere in a refinery. Typical steam cracking feedstocks for propylene production range from LPG to condensates or light naphthas. The naphtha feedstocks common in stem cracking are composed largely of paraffins and cycloparaffins with smaller amounts of aromatics. Gas oil is yet another example of a feedstock which affords a product stream containing both propylene and hydrogen.

A second method of producing propylene is via catalytic cracking; see op. cit, Vol. A18, pp. 61–4 (1991). Chemically, catalytic cracking is analogous to steam cracking in that it is essentially a pyrolytic reaction. However, a catalyst enables cracking (pyrolysis) to occur at lower temperatures, and consequently catalytic cracking is far less energy intensive than steam cracking. Catalytic cracking is essentially the conversion of paraffins and cycloparaffins to materials of lower molecular weight and is characterized by cleavage of carbon-carbon and carbon-hydrogen bonds.

Fluid catalytic cracking (FCC) is an especially important variant of catalytic cracking processes and is the major commercial variant practiced today. See "Handbook of Petroleum Refining Processes," Robert A. Meyers, Editor, pp 2–9 to 2–32. The natural clays, such as montmorillonite, originally used as catalysts were supplanted by various silica aluminas, which in turn have been largely supplanted by zeolitic material. Certainly the contemporary catalysts of choice in FCC are zeolites.

The third major method of propylene production is the catalytic dehydrogenation of propane. See "Ullmann's Encyclopedia of Industrial Chemistry," 5th, Completely Revised Edition, Vol. A22, pp 216–19 (1991). Any method of propane dehydrogenation may be used and is largely a matter of operator's choice. However, that variant known as the Oleflex™ process is our preferred choice. See "Handbook of Petroleum Refining Processes," Robert A. Meyers, Editor, pp 4–23 to 4–28.

In a typical hydrocarbon dehydrogenation process, the feed hydrocarbons (both fresh feed hydrocarbons and recycled unconverted hydrocarbons) are admixed with hydrogen and the resulting admixture is heated by indirect heat exchange with the dehydrogenation reaction zone effluent. After being heated in the feed-effluent heat exchanger, the feed stream is further heated by passage through a heater which is typically a fired heater or furnace. The admixture, typically referred to as the combined feed, is then contacted with a bed of dehydrogenation catalyst, which may exist as a fixed bed, a fluidized bed, or a movable bed via gravity flow. The resulting dehydrogenation zone effluent is withdrawn from the reaction zone and after indirect heat exchange with the combined feed, it is passed to product separation facilities. Generally, the product separation facilities are employed to produce a gas stream, comprising substantially hydrogen, a portion of which may be recycled back to the catalytic reaction zone to provide hydrogen for admixture with the hydrogenatable hydrocarbon feed stream. Generally, a first product stream is produced comprising the desired product olefins and a second product stream comprising light hydrocarbons, typically known as light hydrocarbon by-products, having fewer carbon atoms per molecule than the desired product olefin. Both of these product streams may be recovered in the product separation facilities. In addition, a recycle stream comprising unconverted dehydrogenatable feed hydrocarbons may be withdrawn from the product separation facilities and recycled back into the combined feed stream. Fundamental to the catalytic dehydrogenation process is the fact that the dehydrogenation reaction is highly endothermic which results, as the reaction proceeds, in cooling the reactants to a temperature at which the dehydrogenation reaction will not proceed at any appreciable rate. To counteract this problem, additional heat must be supplied to the bed of dehydrogenation catalyst to assure reaction rates sufficient to make a commercial process economically feasible. Accordingly, many methods of supplying this additional heat have been contrived in order to make catalytic dehydrogenation a viable commercial process.

Many variants of catalysts have been used and are known, although the most effective ones appear to be based on a supported zerovalent platinum or palladium. A range of catalysts used in this process is summarized in U.S. Pat. No. 4,886,928 and U.S. Pat. No. 4,914,075, both of which are hereby incorporated by reference. Several processing variants also are available; see U.S. Pat. No. 4,886,928 for a brief discussion.

The product stream from each of the foregoing processes typically contains components other than propylene and hydrogen and the latter need to be separated in an appropriate fashion. Many separation process variants are available; see "Ullman's Encyclopedia of Industrial Chemistry," Vol. A22, pp 214–6 for several separation techniques applied when the product stream arises in a cracking process. U.S. Pat. No. 5,177,293 describes other separation processes appropriate for the product stream arising in the dehydrogenation of propane. Because recovery of a hydrogen concentrate stream and a propylene rich stream from any of the three propylene production methods discussed above is well known in the art, no detailed description needs to be further elaborated upon.

The hydrogen formed in the propylene production unit is separated, recovered, and purified where necessary for subsequent use in the production of hydrogen peroxide. It is contemplated that the well-known commercial methods of hydrogen recovery will suffice to afford a hydrogen concentrate of sufficient purity for use in hydrogen peroxide manufacture, but if additional purification is required or desired the skilled artisan will know to employ many suitable methods, such as membrane purification, pressure swing adsorption, and so forth. In any event hydrogen peroxide will be produced by direct combination of molecular hydrogen and oxygen or by reaction of molecular oxygen with various hydrogen-containing compounds. The latter is by far the most preferred method of hydrogen peroxide generation, especially when demand is steady and high.

The preferred process to produce hydrogen peroxide in the context of the present invention is based on a reaction cycle comprising autoxidation of 2-alkylanthrahydroquinones. An alkylanthraquinone in solution is catalytically hydrogenated to its corresponding alkylanthrahydroquinone, which subsequently is aerated with an oxygen-containing gas to form hydrogen peroxide and regenerate the alkylanthraquinone. The 2-alkylanthraquinone, for example 2-alkyl-9,10-anthracenediol or 2-alkylanthraquinol, generally is designated as the reaction carrier, hydrogen carder or working material. The solvent for the reactants is called the working solution, and may comprise one or more of alcohols, The reaction carrier preferably is esters, caprolactams, ureas, amides and pyrrolidones. hydrogenated over a palladium catalyst.

Favored industrial 2-antkraquinone carriers include 2-t-amylanthraquinone, 2-s-amylanthraquinone, 2-t-butylanthraquinone and 2-ethylanthraquinone. During hydrogenation of the alkylanthraquinone to its corresponding alkylanthrahydroquinone, the latter may undergo further reduction to a tetrahydroalkylanthrahydroquinone. This compound releases hydrogen peroxide with the formation of a tetrahydroalkylanthraquinone, which can react with the alkylanthrahydroquinone to reform alkylanthraquinone plus tetrahydroalkylanthrahydroquinone, i.e., in a parallel reaction sequence. This latter sequence is a slower reaction, requiring higher temperatures, which is significant in some commercial processes. Various byproducts of the reactions build up in the working solution until purged.

The preferred palladium catalyst used in the hydrogenation reaction may be supported on a carder as a slurry or fixed bed or used as palladium black, wire screen or gauze. Slurry catalysts may be removed and rejuvenated or replaced without a shutdown, but is burdened with suspension difficulties. A fixed catalyst bed requires less stringent feed filtration and avoids inflexibility associated with maintenance of suspension, but requires periodic shutdowns for catalyst rejuvenation or replacement. Hydrogenation operating conditions include a pressure of from about 0.2 to 0.5 MPa absolute and a temperature of up to about 75° C. Minimization of the tetrahydroalkylanthraquinone reaction sequence is favored by lower temperatures in about the 25° to 40° C range. Other considerations in the product of hydrogen peroxide are outlined in, e.g., "Kirk Othmer Encyclopedia of Chemical Technology," Rev. 4, Vol. 13, pp 966–81.

The hydrogen peroxide used in epoxidation of propylene preferably is an aqueous solution. Concentrations of hydrogen peroxide in the reactant mixture typically are less than 10 weight percent, and even about 5 weight percent hydrogen peroxide in the process stream is effective. That the oxidation process is effective with a "working solution" containing under 10 weight percent hydrogen peroxide is quite advantageous and constitutes one of the benefits derived from our invention. As to the relative amounts of hydrogen peroxide and propylene, at a high efficiency of peroxide utilization approximately equal molar amounts of hydrogen peroxide and propylene are preferable. In the most usual case, from about 0.9 to about 1.1 molar proportions of hydrogen peroxide are used per mole of propylene. However, the molar proportions of hydrogen peroxide to propylene may vary between about 0.5 and 2, or even between about 0.2 and about 5.

The hydrogen peroxide as produced is reacted with propylene oxide under epoxidation conditions in the presence of a suitable catalyst. Many catalysts are known for this reaction, including molybdenum-based catalysts. More recently titanosilicate catalysts have been reported to operate quite effectively in the epoxidation of propylene with hydrogen peroxide and they constitute the favored mode in the practice of our integrated process. The use of titanosilicates as an epoxidation catalyst for propylene has been described in U.S. Pat. No. 4,833,260.

More recently an improved titanosilicate, namely a titania-supported titanosilicate, has been described in U.S. Pat. No. 5,354,875 as particularly effective in catalyzing the conversion of propylene to propylene oxide with hydrogen peroxide as the oxidant, especially where the "working solution" (i.e., reactant mixture) contains under 10 weight percent hydrogen peroxide. The materials described therein as catalysts effect conversion of olefins in yields in excess of 90% and with virtually 100% efficiency of hydrogen peroxide utilization. However, it needs to be emphasized that however preferable that particular mode of propylene epoxidation is favored our invention subsumes all modes where hydrogen peroxide serves as the oxidant and propylene is the reactant on which it acts to produce propylene oxide.

FIG. 1 is a flow diagram for the integrated process of our invention and represents some of the many variants which are possible. Although the figure is largely self-explanatory we will give a brief description. The feedstock entering the propylene production unit contains saturated hydrocarbons, normally a mixture of straight and branched-chain alkanes and also may contain naphthenes or cycloparaffins. The propylene production unit itself is generally either a steam cracking unit, a catalytic cracking unit, including an FCC unit, or a propane dehydrogenation unit. The products include propylene, part of which may be used for purposes outside the scope of this invention, other olefins, and hydrogen. The hydrogen formed in the production of propylene is used as one of the reactants, along with oxygen, in the hydrogen peroxide unit. As indicated in our example, it is likely that the hydrogen accompanying the formation of propylene is insufficient to make the requisite mount of hydrogen peroxide necessary for the epoxidation of propylene, consequently additional hydrogen needs to be imported. Some of the hydrogen peroxide produced may be used independently, but it is contemplated that most, if not all, of the hydrogen peroxide production will be used to oxidize propylene in the propylene oxide unit. Water that accompanies the epoxidation of propylene is returned from the propylene oxide unit to the hydrogen peroxide unit and the product propylene oxide is recovered.

The following example is merely illustrative of our invention and is not intended to restrict it in any way.

EXAMPLE 1

The following represents mass balances required for the production of 100,000 metric tons of propylene oxide. The theoretical amounts, given in metric tons, assume 100% reaction. The actual amounts projected are based on yields given in parentheses following the amounts.

TABLE 1

| Requirements for Production of 100 Metric Tons of Propylene Oxide | | |
|---|---|---|
| | Theoretical[a] | Actual[b] |
| Propylene (100% pure) | 72,452 | 73,931 (98%) |
| Hydrogen Peroxide (100% pure) | 58,567 | 61,649 (95%) |
| To produce 100% pure $H_2O_2$ | | |

TABLE 1-continued

| | Requirements for Production of 100 Metric Tons of Propylene Oxide | |
|---|---|---|
| | Theoretical[a] | Actual[b] |
| requires | | |
| a) for 58,567 metric tons | | |
| $H_2$ (100%) | 3471 | 3951 (88%) |
| $O_2$ | 55,096 | |
| b) for 61,649 metric tons | | |
| $H_2$ (100%) | 3654 | 4159 (88%) |
| To produce 100% pure propylene requires | | |
| a) for 72,452 metric tons | | |
| propane (100%) | 75,923 | 86,129 (88%) |
| $H_2$ (100%) - net from separation[c] | 3471 | 2306 |
| b) for 73,931 metric tons | | |
| propane (100%) | 77,473 | 87,887 |
| $H_2$ (100%) - net from separation[c] | 3542 | 2353 |

[a]Amounts, in metric tons, for 100% utilization
[b]Amounts, in metric tons, for actual utilization based on yield or conversion given in parentheses.
[c]Net pure hydrogen obtained after separation via pressure swing adsorption.

This table shows that production of 100,000 metric tons of propylene likely requires 61,649 metric tons $H_2O_2$, which in turn requires about 4159 metric tons hydrogen. However, formation of 73,931 metric tons propylene will afford only about 2,353 metric tons hydrogen. Consequently, additional hydrogen will need to be furnished to the hydrogen peroxide unit if all of the propylene produced is epoxidized. Of course, part of the propylene produced may be diverted to other uses, in which case additional hydrogen needs are reduced.

What is claimed is:

1. An integrated process for the production of propylene oxide from saturated hydrocarbons comprising:

a. producing from a saturated hydrocarbon-containing feedstock a product stream containing propylene and hydrogen;

b. separating said product stream into a propylene-rich stream and a hydrogen-rich stream;

c. processing hydrogen in the hydrogen-rich stream in a peroxidation zone at peroxidation conditions to obtain hydrogen peroxide;

d. epoxidizing in an epoxation zone the propylene in the propylene-rich stream with hydrogen peroxide in the presence of an epoxation catalyst at epoxation conditions to form propylene oxide; and e. recovering the propylene oxide formed.

2. The process of claim 1 where formation of the product stream is effected by dehydrogenation of a propane-containing stream.

3. The process of claim 1 where formation of the product stream is effected by steam cracking.

4. The process of claim 1 where formation of the product stream is effected by catalytic cracking.

5. The process of claim 4 where formation of the product stream is effected by fluid catalytic cracking.

6. The process of claim 1 where hydrogen peroxide is produced by autoxidation of 2-alkylanthrahydroquinones.

7. The process of claim 1 where the epoxation catalyst is a titanosilicate.

8. The process of claim 7 where the titanosilicate is a titania-supported titanosilicate.

9. The process of claim 1 where the propylene is epoxidized with hydrogen peroxide and the reaction solution contains hydrogen peroxide at a concentration not more than about 10 weight percent.

10. The process of claim 1 further characterized in that an external hydrogen stream supplements the hydrogen-rich stream in the peroxidation zone.

* * * * *